(12) United States Patent
Nair et al.

(10) Patent No.: US 6,316,228 B1
(45) Date of Patent: Nov. 13, 2001

(54) EFFICIENT SYNTHESIS OF NUCLEOSIDES

(75) Inventors: Vasu Nair; Suresh Pal, both of Iowa City, IA (US)

(73) Assignee: The University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/341,473

(22) PCT Filed: Oct. 20, 1997

(86) PCT No.: PCT/US97/18239

§ 371 Date: Jul. 12, 1999

§ 102(e) Date: Jul. 12, 1999

(87) PCT Pub. No.: WO98/17781

PCT Pub. Date: Apr. 30, 1998

Related U.S. Application Data

(60) Provisional application No. 60/029,446, filed on Oct. 21, 1996.

(51) Int. Cl.⁷ .............................. C12P 19/38; C12N 1/00; C12N 1/20

(52) U.S. Cl. .............................................. 435/87; 822/832

(58) Field of Search ................................ 435/87, 832, 822

(56) References Cited

U.S. PATENT DOCUMENTS 5,258,301 * 11/1993 Yamauchi et al. ................ 435/252.5

FOREIGN PATENT DOCUMENTS 4-197193 * 7/1992 (JP) .
5-49493 * 3/1993 (JP) .

OTHER PUBLICATIONS

Morisawa et al. Tetrahedron Letters. 1980. vol. 21, pp. 479–482.*

* cited by examiner

*Primary Examiner*—Vera Afremova
(74) *Attorney, Agent, or Firm*—Foley & Ladner

(57) ABSTRACT

Methods and compositions, including cell cultures, for producing nucleosides are provided which comprise contacting a nucleoside precursor and a sugar moiety donor with a cell containing a nucleoside phosphorylase. The nucleoside precursor can be a purine or pyrimidine base and the sugar moiety donor can comprise a ribose, a deoxyribose, including 2-deoxyribose, or other sugar of choice. The methods and composition can be used to make thymidine from thymine and 2-deoxyinosine or 2'-deoxyadenosine. Other nucleosides, including those having anticancer and/or antiviral properties, also can be obtained according to the invention.

23 Claims, 1 Drawing Sheet

US 6,316,228 B1

EFFICIENT SYNTHESIS OF NUCLEOSIDES

This application is a 371 of PCT/US97/18239 filed Oct. 20, 1997, which in turn, claims priority to U.S. Provisional Application No. 60/029,446 filed Oct. 21, 1996.

The present invention relates to the efficient and general synthesis of nucleosides, including thymidine, with whole bacterial cells.

BACKGROUND OF THE INVENTION

Nucleoside phosphorylases, which can be found in bacteria and other organisms, catalyze the reversible phosphorolysis of nucleosides and the transferase reaction involving purine and pyrimidine bases. Purine and pyrimidine nucleoside phosphorylases have been isolated from a number of bacterial cells. Utagawa et al., *FEBS Lett.* 109: 261–63 (1980); Utagawa, et al., *Agri. Biol. Chem.* 49: 3239–46 (1985); Engelbrecht, et al., *J. Biol. Chem.* 244: 6228–32 (1969); Jensen, *Eur. J. Biochem.* 61: 377–86 (1976); Jensen, et al., *Eur. J. Biochem.* 51: 253–65 (1975). For example, uridine phosphorylase, thymidine phosphorylase and purine nucleoside phosphorylase have been purified from *Escherichia coli*. Krenitsky et al., *Biochemistry* 20: 3615–21 (1981); Schwartz, et al., *Eur. J. Biochem.* 21: 191–98(1971). Additionally, a thermostable purine nucleoside phosphorylase enzyme has been isolated from *Bacillus stearothermophilus*. Saunders, et al., *J. Biol. Chem.* 244. 3691–97 (1969); Hori et al., *Agric. Biol. Chem.* 53: 2205–2210 (1989).

These nucleoside phosphorylases possess fairly broad substrate specificity and have been utilized in the synthesis of natural and modified ribonucleoside analogs. Shirae et al., *Agric. Biol. Chem.* 52: 1499–1504 (1988); Hennen et al., *J. Org. Chem.* 54:4692–95 (1989); Hori et al., *Agric. Biol. Chem.* 55: 1071–1074 (1991); Hori et al., *J. Biotech.* 17: 121–131 (1991); Hori et al., *Biosci. Biotech. Biochem.* 56: 580–582 (1992). There are fewer examples of the use of whole cells in the synthesis of nucleosides, particularly 2'-deoxynucleosides. Morisawa et al., *Tetrahedron Lett.* 21: 479–482 (1980); Holy et al., *Nucleic Acid Research Symposia* 18:69–72 (1987). Morisawa et al. used a combination of *Enterobacter aerogene* cells and chemical steps to synthesize arabinofuranosyl purine nucleosides. Holy et al. used *E. coli* cells and 2'-deoxyuridine as substrate to synthesize 2'-deoxy purine and pyrimidine nucleosides, but *E. coli* cannot be used above physiological temperatures.

Several nucleosides have important diagnostic and therapeutic uses. For example, the natural 2'-deoxynucleoside, thymidine, is a precursor for the synthesis of a number of important anti-HIV active nucleosides such as 3'-deoxy-3'azidothymidine (AZT) and dideoxydidehydrothymidine (d4T) and various potential antiviral compounds. Thymidine and other deoxynucleosides (both natural and non-natural) are precursors of certain oligomers referred to as "anti-sense oligonucleotides," many of which are being investigated as drugs against viruses, tumors and bacterial infections.

Yet thymidine and other deoxynucleosides are relatively expensive and difficult to obtain by known approaches. For example, prior to the present invention, thymidine was produced by the hydrolysis of DNA derived from natural sources, like milt, but there are limitations using this approach. Dekker et al., *J. Chem. Soc.* 947–55 (1953). Chemical methods also are available for the synthesis of thymidine, but these involve complex, multi-step methodologies.

For example, an early chemical synthesis of thymidine involves a multi-step procedure which gave very low overall yields of thymidine (<5%). Shaw et al., *Proc. Chem. Soc.* 81–82 (1958); Shaw et al., *J. Chem. Soc.* 50–55 (1959). A more direct chemical method involves coupling of suitably protected thymine with an α-chloro-2-deoxy sugar. Hubbard et al., *Nucleic Acids Res.* 12: 6827–36 (1984). While the coupling step proceeds in good yields, the desired β-thymidine derivative is produced together with its α-isomer and separation of the desired β-isomer requires extensive chromatography. In addition, suitably protected bases have to be prepared for the coupling. Also, the α-chloro sugar for the coupling reaction is unstable and has to be carefully prepared and handled. Thus, the overall yield of thymidine by this method is low. A multi-step synthesis of thymidine from D-xylose also has been reported. Rao et al., *Proc. Ind. Acad. Sci. (Chem. Sci.)* 106:1415–21 (1994). However, the overall yield in this case is only 24% and the synthesis involves the use of some difficult to handle reagents (e.g. $SnCl_4$). Morisawa et al., *Tetrahedron Lett.* 21: 479–482 (1980) used a combination of *Enterobacter aerogene* cells and chemical steps to synthesize a few arabinofuranosyl purine nucleosides. However, the yield in the enzymatic step alone was merely 34% and only arabinofuranosyl purine nucleosides were synthesized. Holi et al., *Nucleic Acid Research Symposia* 18: 69–72 (1987) used *E. coli* cells and only 2'-deoxyuridine as substrate to synthesize only 2'-deoxy purine and pyrimidine nucleosides. Holi et al. reported that the % conversion to thymidine was 67% in their synthesis. The disadvantage of the approach of Holi et al. include the use of 2'-deoxyuridine, which is expensive relative to other substrates. Additionally, their reliance upon *E. coli* limits the reaction temperature, which leads to slower reaction kinetics and decreased solubilities of reactants and products.

Accordingly, there is a need for improved methods for producing thymidine and other deoxynucleosides that have broad range applications, including the production of other natural and non-natural nucleosides. Due to the societal importance of these nucleosides, there is needed methods capable of being undertaken on an industrial scale. These needs have been unresolved until the advent of the present invention.

SUMMARY OF THE INVENTION

It is an object of the present invention to provide methods and compositions, including cultures, to produce nucleosides.

It is another object to produce nucleosides from nucleoside precursors and sugar moiety donors.

It is still another object to produce nucleosides with cells, including bacterial cells.

In accomplishing these and other objects, there are provided, in accordance with one aspect of the present invention, methods for producing a nucleoside, comprising the steps of contacting a nucleoside precursor and a sugar moiety donor with a whole cell containing a nucleoside phosphorylase in order to produce the nucleoside, and obtaining the nucleoside from the cell. Xanthine oxidase and the like can be present at this stage, which can shift the reaction equilibrium to the product side.

The nucleoside precursor can be a purine or pyrimidine base and the sugar moiety donor can comprise a ribose, a deoxyribose (including 2-deoxyribose), or other sugar of choice. The nucleoside phosphorylase can be a purine nucleoside phosphorylase or a pyrimidine nucleoside phosphorylase, depending upon the sugar moiety donor. The cell can be any type of cell capable of performing the reactions. The cell can be a bacterial cell, such as *Bacillus stearothermophilus* cells. In accordance with one embodiment, the base is thymine, the sugar moiety donor is 2'-deoxyinosine, and the nucleoside phosphorylase is a purine nucleoside phosphorylase. 2'-Deoxyinosine can be produced in situ from the reaction of adenosine deaminase on 2'-deoxyadenosine.

Depending upon the starting compounds, both natural and non-natural nucleosides can be produced according to the invention. Anticancer nucleosides, such as 5-fluorouracildeoxyriboside (5-FUDR), 5-azacytidine, cytosine arabinoside, arabino-5-azacytidine (Ara-AC) can is be obtained according to the invention. Moreover, nucleoside precursors of therapeutically useful compounds, as the anti-HIV compounds, AZT and dideoxydidehydrothymidine (d4T), can be produced according to the invention.

The invention can employ cytosine, thymine or uracil as a pyrimidine base or adenine and guanine as a purine base, 2'-deoxyinosine as a sugar moiety donor, and purine nucleoside phosphorylase. A pyrimidine nucleoside phosphorylase can be used where the sugar moiety donor is a pyrimidine nucleoside, such as 2'-deoxycytidine.

Pyrimidine bases can be selected from, but are not restricted to, the group consisting of 5-fluorouracil, 5-chlorouracil, 5-iodouracil, and 5-azacytosine. Purine bases can be selected from, but are not restricted to, the group consisting of 2,6-diaminopurine, 2-amino-6-iodopurine, 2,6-dichloropurine, 6-thioguanine, 6-iodopurine, 6-chloropurine, 8-azaadenine, allopurine, and isoguanine. These bases can be used with the same or different sugar moiety donors and nucleoside phosphorylases. For example, sugar moiety donors include purine ribonucleosides (for example, inosine), purine deoxynucleosides (for example, 3'-deoxyinosine), pyrimidine ribonucleosides (for example, cytidine), pyrimidine deoxynucleosides (for example, 2'-deoxycytidine), and arabinonucleosides.

In accordance with another aspect of the present invention, there is provided a cell culture for producing a nucleoside, comprising a culture medium comprising a nucleoside precursor and a sugar moiety donor, and a whole cell containing a nucleoside phosphorylase. The nucleoside precursor can be a purine or pyrimidine base and the sugar moiety donor can comprise a ribose, a deoxyribose, including 2-deoxyribose, or other sugar of choice. The nucleoside phosphorylase can be a purine nucleoside phosphorylase or a pyrimidine nucleoside phosphorylase. The cell can be any type of cell capable of performing the reactions. The cell can be a bacterial cell, such as a *Bacillus stearothermophilus* cell. In accordance with one embodiment, the base is thymine, the sugar moiety donor is 2'-deoxyinosine, and whole cell containing the nucleoside phosphorylase is *Bacillus stearothermophilus*.

In accordance with yet another aspect of the present invention, there is provided a method of producing thymidine, comprising the steps of contacting thymine and 2'-deoxyinosine with a cell containing a purine nucleoside phosphorylase in order to produce said thymidine, and obtaining thymidine from the cell. The cell can be any type of cell capable of performing the reactions. The cell can be a bacterial cell, such as a *Bacillus stearothermophilus* cell. The invention has many applications and uses.

In accordance with a further aspect of the invention, there are provided methods for producing thymidine, comprising the step of contacting at least one type of 2'-deoxynucleoside with *Bacillus stearothermophilus* cells, thymine, and at least one sugar moiety donor selected from the group consisting of 2'-deoxyadenosine, 2'-deoxyguanosine, and 2'-deoxycytidine.

These and other aspects of the present invention will become apparent to the person of skill in the art in view of the teachings contained herein. The invention disclosed herein encompasses biotechnological inventions, including biotechnological processes.

DETAILED DESCRIPTION OF PREFERRED EMBODIMENTS

Figure 1:
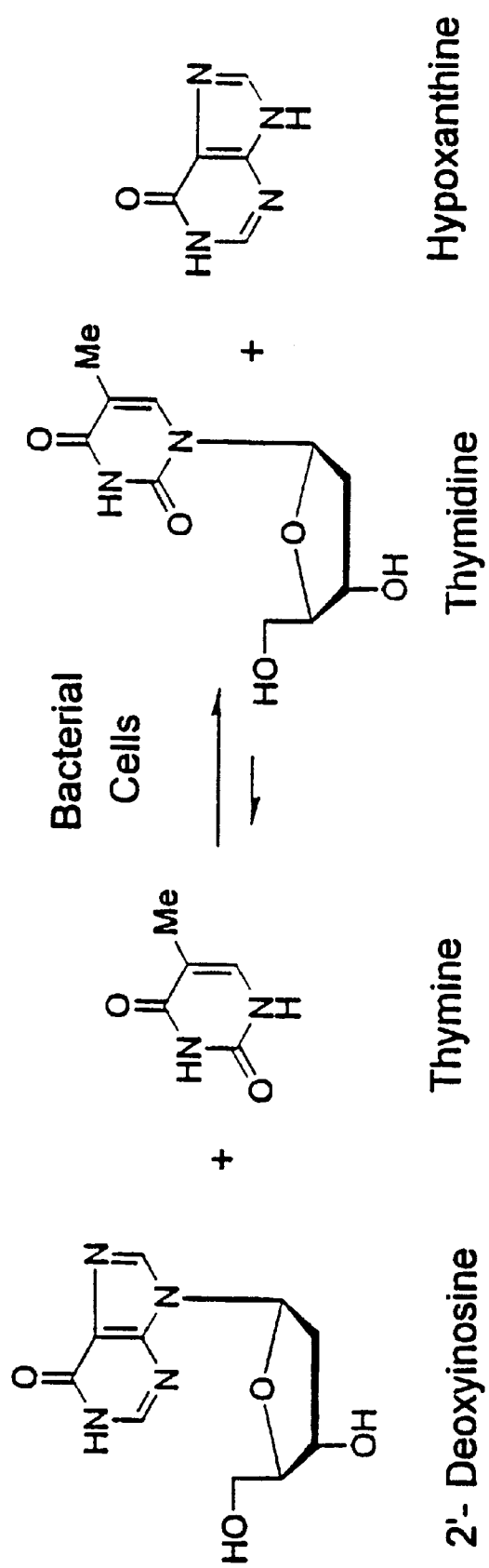
FIG. 1 schematically depicts the bacterial-mediated reaction between 2'-deoxyinosine and thymine to form thymidine and hypoxanthine.

The present invention relates to the use of bacteria, preferably whole cells, for the efficient synthesis of nucleosides. As used herein, nucleosides refer to purine bases, pyrimidine bases and the like attached to a sugar moiety, including riboses and deoxyriboses.

According to the present invention, a nucleoside can be produced by a nucleoside precursor and a sugar moiety donor with a cell containing nucleoside phosphorylases in order to produce the nucleoside. The nucleoside precursor can be a purine or pyrimidine base and the sugar moiety donor can comprise a ribose, a deoxyribose, including 2-deoxyribose, 3-deoxyribose, arabinose or other sugar of choice. The nucleoside phosphorylase can be a purine nucleoside phosphorylase or a pyrimidine nucleoside phosphorylase, as present in the cell. The cell can be a bacterial cell, such as a *Bacillus stearothermophilus* cell.

The present invention allows surprisingly simpler and more efficient production of the biologically and industrially important compound, thymidine, as well as other nucleosides. Thymidine can be produced by using 2'-deoxyinosine (either directly or through its generation from 2'-deoxyadenosine by the activation of adenosine deaminase) and thymine as substrates. Many other natural and non-natural nucleosides can be synthesized using the present invention because the invention can employ any type of purine or pyrimidine base (including natural and non-natural bases) and any type of sugar moiety (including ribose, deoxyribose, arabinose, or other appropriate carbohydrates) as precursors. Suitable bacteria for use with the present invention include *Bacillus stearothermophilus*, which is a thermostable bacteria. The *Bacillus stearothermophilus* cells can be used repeatedly without appreciable loss of activity.

In the process according to the invention, the 2'-deoxyribose moiety of 2'-deoxyinosine was transferred from 2'-deoxyinosine to thymine by the transdeoxyglycosylation activity of bacterial cells. A conversion rate of over 70% can be obtained.

*Bacillus stearothermophilus* can be used according to the invention. The advantage of *B. stearothermophilus* is that it can be used at temperatures well above room temperature (for example, about 55° C.), where the solubility of thymine is much higher than at room temperature (about 25° C.). The reaction can be conducted over a broad pH range of about 4.0 to 8.0, with an optimum pH of about 5.2. A decrease in activity is usually found with *B. stearothermophilus* at the stronger alkaline pH levels.

The maximum yield of thymidine is obtained when substrates (2'-deoxyinosine and thymine for thymidine production) are used in equal concentrations. The inclusion of xanthine oxidase in the reaction can surprisingly increase the conversion percentage to 90% or greater.

The preparation of thymidine by biotransformation with whole cells is an attractive alternative to pre-existing methodologies, which are much less efficient and/or cumbersome. Because of the ready diffusion of substrates into these bacterial cells, the whole cells could be used for the transdeoxyribosylation between activated 2'-deoxyinosine and unactivated thymine base to yield thymidine. The present invention also allows the production of other nucleosides, both natural and non-natural.

The invention is further described by the following examples, which do not limit the invention in any way.

EXAMPLE I

Growth and Assay of Bacteria Cells

Bacteria

*Bacillus stearothermophilus*

Tryptic soy broth medium was prepared by dissolving 30 g of tryptic soy broth (17 g Bacto peptone, 3 g Bacto soytone, 2.5 g of dextrose, 5 g of sodium chloride, 2.5 g of dipotassium phosphate) in 1000 ml water. One vial of *B. stearothermophilus* (ATCC 12980) was taken up in 1 ml of tryptic soy broth medium and then transferred to 50 ml of tryptic soy broth medium. This culture was grown overnight at 55° C. and then 10 ml of the resulting culture was inoculated in 1.5 liter of tryptic soy broth medium and growth was monitored for 12 h at 55° C. The cells were harvested at 4° C. at 6000 r.p.m. A total of 4 g (wet weight) of cells were obtained from 6 liters.

Assays

The assay reactions were carried out at 55° C. for in 50 mM ammonium acetate buffer (10 ml) at pH 5.2 with 2.0 g (wet weight) *B. stearothermophilus* cells and 5 mM 2'-deoxyinosine and 5 mM thymine. HPLC on an analytical delta-pak C-18 column (3.9×300 mm) was used for the separation and identification of product. Development was carried out by isocratic elution with 5 mM phosphate buffer (pH 4.5) containing 5% methanol.

EXAMPLE II

Production of Thymidine Using Bacterial Cells

The transdeoxyribosylation reaction with *Bacillus stearothermophilus* was carried out with 5 mM 2'-deoxyinosine and 5 mM thymine and reached equilibrium in 1 hour. See FIG. 1.

The assay mixture contained 2 g (wet weight) of *Bacillus stearothermophilus* cells, 5 mM 2'-deoxyinosine and 5 mM thymine in 10 ml of 50 mM ammonium acetate buffer (pH 5.5). The conversions were run at 55° C. for 1 hour. The reaction mixture was centrifuged and then filtered using an Amicon Ultrafiltration device (YM-3 membrane) and the products were separated and analyzed by HPLC (C-18 column) in 5% methanol and 5 mM phosphate buffer at pH 4.6 using a flow rate of 0.5 ml/min. Blanks were run to check the authenticity of the reaction. No undesirable side reactions were detected. Thymidine was obtained in 56% yield (78% conversion).

The advantage of carrying out the transformations at 55° C. is that the solubility of thymine is higher at 55° C. than at room temperature, which is an important consideration in scale-up towards industrial production. These bacterial cells could be used repeatedly without appreciable loss of activity.

The effect of pH on reaction rates also was examined. While the bacterial cells have activity over a broad pH range (approximately 4.0 to 8.0), the yield of product varied within this pH range with the optimum pH being 5.2. Activity over a broad pH range is consistent with the observation that several different kinds of phosphorylases with different pH optima for PNPase (nucleoside phosphorylases) activity have been found in *B. stearothermophilus* JTS 859. Hori et al., *Agric. Biol. Chem.* 53: 2205–2210 (1989); Hori et al., *J. Biotech.* 17: 121–131 (1991).

The effects of substrate concentrations also were investigated. The assay mixture contained 1 g (wet weight) of *B. stearothermophilus* cells, 5 mM thymine, and varying concentrations of 2'-deoxyinosine in 5 ml of 50 mM ammonium acetate buffer (pH 5.5). The assays were carried out for 2 hours at 55° C.

When the concentration of thymine was kept constant and the concentration of 2'-deoxyinosine was changed, it was discovered that equal concentrations of both substrates give rise to the optimum product yield.

The reactions also were carried out in a 40% ethanol/aqueous buffer. The solubility of thymine is five times higher in a 40% ethanol/aqueous buffer than the solubility in an aqueous buffer. The use of the ethanol/aqueous buffer resulted in a 28% yield (47% conversion).

Although the invention is not limited to any particular theory or mechanism, it appears that the overall cellular transformation depends upon the internal phosphorylation of the 2'-deoxyribose moiety in the phosphorolysis step. After this first step, the phosphorylated intermediate is trapped inside the cell. Activity of the cells to catalyze the two steps (phosphorolysis and transferase) of this synthesis as measured by the amount of thymidine produced reached a maximum in 1 hour and then decreased as time increased. However, after the reaction, these cells could be separated and used repeatedly without appreciable loss of activity. The cells also produced hypoxanthine from 2'-deoxyinosine in the reaction. HPLC analysis of the reaction mixture did not reveal the presence of uric acid from the oxidation of hypoxanthine, however.

Surprisingly, the optimum pH for the cellular enzymatic synthesis was 5.2 compared to the optimum with the isolated enzyme, PNPase, which was close to 7.

EXAMPLE III

Production of Thymidine Using Bacterial Cells with 2'-Deoxyadenosine as Statring Substrate 2'-Deoxyadenosine (5 mM) was deaminated to 2'-deoxyinosine with excess adenosine deaminase in acetate buffer (pH 5.5). The reaction mixture was filtered with an Amicon Ultrafiltration device (YM-3 membrane) and the transdeoxyribosylation reaction was then carried out at 55° C. and the product isolated as described in Example II. Thymidine was obtained in 56% yield (80% conversion).

EXAMPLE IV

Production of Thymidine Using Bacterial Cells and Xanthine Oxidase

The assay mixture contained 2 g (wet weight) of *Bacillus stearothermophilus* cells, 5 mM 2'-deoxyinosine, 5 mM thymine, 20 units of xanthine oxidase (from buttermilk) in 10 ml of 50 mM ammonium acetate buffer (pH 5.5). The conversions were run at 55° C. for 1 hour. The reaction mixture was centrifuged and then filtered using an Amicon Ultrafiltration device (YM-3 membrane) and the products were separated and analyzed by HPLC (C-18 column) in 5% methanol and 5 mM phosphate buffer at pH 4.6 using a flow rate of 0.5 ml/ min. Thymidine was isolated in 68% yield (90% conversion).

The use of xanthine oxidase had the effect of shifting the equilibrium to the product side by removing hypoxanthine from the reversible biotransformation. When xanthine oxidase was used with the cellular transformation, the yield of thymidine increased unexpectedly high as compared to Example II.

EXAMPLE V

Production of Thymidine Using Bacterial Cells and a Pyrimidine Deoxynucleoside as Substrate The assay was carried out as described in Example II, except that 2'-deoxycytidine was used as substrate in place of 2'-deoxyinosine. Thymidine was obtained in 44% yield (70% conversion).

EXAMPLE VI

Conversion of a Mixture of Deoxynucleosides to Thymidine Using Bacterial Cells

The assay was carried out as described in Example II, except that a mixture of 2'-deoxycytidine, 2'-deoxyadenosine and 2'-deoxyguanosine were used as substrates in place of 2'-deoxyinosine. Thymidine was obtained in 54% yield (about 60% conversion).

EXAMPLE VII

Synthesis of Non-Natural Deoxynucleosides Using Bacterial Cells

Many non-natural deoxynucleosides can be synthesized using the whole cell procedure according to the present invention. Two examples are presented here to illustrate the procedure.

(a) The assay mixture contained 2 g (wet weight) of *Bacillus stearothermophilus cells,* 5 mM 2'-deoxyinosine and 5 mM 2,6-diaminopurine in 10 ml of 50 mM ammonium acetate buffer (pH 5.5). The conversions were run at 55° C. for 5 hour. The reaction mixture was centrifuged and then filtered using an Amicon Ultrafiltration device (YM-3 membrane) and the products were separated and analyzed by HPLC (C-18 column) in 5% methanol and 5 mM phosphate buffer at pH 4.6 using a flow rate of 0.5 ml/min. Blanks were run to check the authenticity of the reaction. No undesirable side reactions were detected. 2,6-diaminopurine 2'-deoxynucleoside was obtained in 60% yield (80% conversion).

(b) An assay mixture containing 2 g (wet weight) of *Bacillus stearothermophilus cells,* 5 mM 2'-deoxyinosine and 5 mM 5-fluorouracil was made in 10 ml of 50 mM ammonium acetate buffer (pH 5.5). The conversions were run at 55° C. for 5 hour. The reaction mixture was centrifuged and then filtered using an Amicon Ultrafiltration device (YM-3 membrane) and the products were separated and analyzed by HPLC (C-18 column) in 5% methanol and 5 mM phosphate buffer at pH 4.6 using a flow rate of 0.5 ml/min. Blanks were run to check the authenticity of the reaction. No undesirable side reactions were detected. 5-fluoro-2'-deoxyuridine was obtained in 30% yield (62% conversion).

It is to be understood that the description, specific examples and data, while indicating preferred embodiments, are given by way of illustration and exemplification and are not intended to limit the present invention. Various changes and modifications within the present invention will become apparent to the person of skill in the art from the discussion and disclosure contained herein.

What is claimed is:

1. A method for producing a nucleoside in a single reaction mixture, comprising the steps of:
    (i) contacting, in said reaction mixture, a nucleoside precursor, xanthine oxidase, and a sugar moiety donor selected from the group consisting of 2'-deoxyinosine, inosine, arabinonucleoside, and 3'-deoxyinosine with a whole cell containing a nucleoside phosphorylase to produce said nucleoside, wherein cleavage of said nucleoside precursor by said nucleoside phosphorylase occurs inside of said whole cell to produce said nucleoside and hypoxanthine, and wherein oxidation of hypoxanthine by xanthine oxidase occurs outside of said whole cell, thereby shifting the equilibrium to the formation of said nucleoside by removal of hypoxanthine from reversible biotransformation; and
    (ii) obtaining said nucleoside from said whole cell.

2. A method according to claim 1, wherein said nucleoside precursor is a pyrimidine base.

3. A method according to claim 2, wherein said pyrimidine base is thymine, and wherein said nucleoside phosphorylase is a purine nucleoside phosphorylase.

4. A method according to claim 2, wherein said pyrimidine base is cytosine or uracil, and wherein said nucleoside phosphorylase is a purine nucleoside phosphorylase.

5. A method according to claim 2, wherein said pyrimidine base is selected from the group consisting of 5-fluorouracil, 5-chlorouracil, 5-iodouracil, and 5-azacytosine, and wherein said nucleoside phosphorylase is a purine nucleoside phosphorylase.

6. A method according to claim 1, wherein said nucleoside precursor is a purine base.

7. A method according to claim 6, wherein said purine base is adenine or guanine, and wherein said nucleoside phosphorylase is a purine nucleoside phosphorylase.

8. A method according to claim 6, wherein said purine base is selected from the group consisting of 2,6-diaminopurine, 2-amino-6-chloropurine, 2,6-dichloropurine, 6-thioguanine, 6-iodopurine, 6-chloropurine, 8-azaadenine, allopurine, and isoguanine, and wherein said nucleoside phosphorylase is a purine nucleoside phosphorylase.

9. A method according to claim 1, wherein said whole cell is a bacterial cell.

10. A method according to claim 9, wherein said bacterial cell is a *Bacillus stearothermophilus* cell.

11. A cell culture for producing a nucleoside in a single reaction mixture, comprising: (i) a culture medium comprising a nucleoside precursor, xanthine oxidase, and a sugar moiety donor selected from the group consisting of 2'-deoxyinosine, inosine, arabinonucleoside, and 3'-deoxyinosine, and: (ii) a whole cell containing a nucleoside phosphorylase.

12. A cell culture according to claim 11, wherein said nucleoside precursor is a pyrimidine base.

13. A cell culture according to claim 12, wherein said pyrimidine base is thymine, and wherein said nucleoside phosphorylase is a purine nucleoside phosphorylase.

14. A cell culture according to claim 11, wherein said whole cell is a bacterial cell.

15. A cell culture according to claim 14, wherein said bacterial cell is a *Bacillus stearothermophilus* cell.

16. A method for producing thymidine in a single reaction mixture, comprising the steps of:

(i) contacting, in said reaction mixture, thymine, xanthine oxidase, and 2'-deoxyinosine with a whole cell containing a purine nucleoside phosphorylase to produce said thymidine, wherein cleavage of said thymine by said purine nucleoside phosphorylase occurs inside of said whole cell to produce said thymidine and hypoxanthine, and wherein oxidation of hypoxanthine by xanthine oxidase occurs outside of said whole cell, thereby shifting the equilibrium to the formation of said thymidine by removal of hypoxanthine from reversible biotransformation; and (ii) obtaining said thymidine from said whole cell.

17. A method according to claim 16, wherein said whole cell is a *Bacillus stearothermophilus* cell.

18. A method according to claim 1, wherein said sugar moiety donor is 2'-deoxyinosine produced in situ from the reaction of adenosine deaminase on 2'-deoxyadenosine.

19. A method according to claim 1, wherein said sugar moiety donor is inosine and wherein said produced nucleoside is a ribonucleoside.

20. A method according to claim 1, wherein said sugar moiety donor is an arabinonucleoside, and wherein said produced nucleoside is an arabinoside.

21. A method according to claim 1, wherein said sugar moiety donor is 3'-deoxyinosine and wherein said produced nucleoside is a 3'-deoxynucleoside.

22. A method according to claim 1, wherein said sugar moiety donor is 2'-deoxyinosine.

23. A cell culture according to claim 11, wherein said sugar moiety donor is 2'-deoxyinosine.

* * * * *